United States Patent [19]

Banholzer

[11] Patent Number: 4,549,021
[45] Date of Patent: Oct. 22, 1985

[54] N-(β-FLUOROETHYL)-NORTROPINE

[75] Inventor: Rolf Banholzer, Ingelheim am Rhein, Fed. Rep. of Germany

[73] Assignee: Boehringer Ingelheim KG, Ingelheim am Rhein, Fed. Rep. of Germany

[21] Appl. No.: 612,790

[22] Filed: May 22, 1984

[30] Foreign Application Priority Data

Jun. 3, 1984 [DE] Fed. Rep. of Germany ....... 3320138

[51] Int. Cl.$^4$ ............................................. C07D 451/06
[52] U.S. Cl. ........................................ 546/127; 546/129
[58] Field of Search ................. 546/127, 131; 424/265

[56] References Cited

U.S. PATENT DOCUMENTS 3,505,337  4/1970  Zeile et al. ........................... 260/292
4,042,700  8/1977  Banholzer et al. ................... 424/265
4,486,441 12/1984  Fozard et al. ........................ 424/265

Primary Examiner—Henry R. Jiles
Assistant Examiner—Barbara Cassatt
Attorney, Agent, or Firm—Hammond & Little, Weissenberger & Dippert

[57] ABSTRACT

The compound of the formula

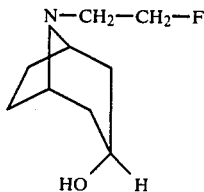

and acid addition salts thereof. The compounds are useful as intermediates for the preparation of N-(β-fluoroethyl)-nortropine benzilate.

1 Claim, No Drawings

N-(β-FLUOROETHYL)-NORTROPINE

This invention relates to a novel derivative of nortropine and acid addition salts thereof, to methods of preparing these compounds and to methods of using them as intermediates for the preparation of pharmaceuticals.

More particularly, the present invention relates to the novel compound N-(β-fluoroethyl)-nortropine of the formula

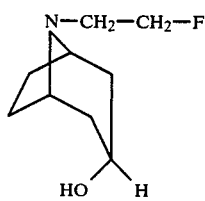

and acid addition salts thereof.

N-(β-fluoroethyl)-nortropine may be prepared by the following methods:

Method A

By alkylating nortropine or a salt thereof with a compound of the formula

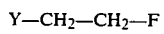

wherein Y is a leaving group, preferably halogen. A preferred alkylating agent of the formula II is 1-fluoro-2-bromo-ethane, which may be prepared by the method of F. L. M. Pattison et al., J.Org.Chem. 21, 748 (1956).

The N-alkylation reaction is performed under conditions which are conventional for N-alkylation of a secondary amine.

Methods of preparation of nortropine and salts thereof are described in the literature. See, for example, the following: T. D. Perrine, J.Org.Chem. 16, 1303 (1951), S. P. Findlay, J.Amer.Chem.Soc. 75, 3204 (1953), and G. Kraiss and K. Nádor, Tetrahedron Letters (London) 1971, (1) 57.

Method B

By selectively hydrogenating N-(β-fluoroethyl)-nortropinone in the presence of a suitable catalyst, such as Raney nickel, to form the corresponding 3-α-ol.

The starting compound, N-(β-fluoroethyl)-nortropinone, may be prepared either by alkylating nortropinone or a salt thereof with a 1-fluoro-2-halo-ethane such as 1-fluoro-2-bromo-ethane, or by the Robinson-Schöpf reaction with 1-fluoro-2-amino-ethane.

N-(β-Fluoroethyl)-nortropine is basic and therefore forms addition salts with inorganic or organic acids. Examples of non-toxic, pharmacologically acceptable acid addition salts are hydrochloric acid, hydrobromic acid, sulfuric acid or oxalic acid or the like.

The following example illustrates the present invention and will enable others skilled in the art to understand it more completely. It should be understood, however, that the invention is not limited solely to the particular example given below.

EXAMPLE 1

N-(β-Fluoroethyl)-nortropine and its hydrochloride

A mixture of 33.8 g (0.2657 mol) of nortropine, 37.1 g (0.2922 mol) of 2-bromo-1-fluoro-ethane, 31.0 g (0.2922 mol) of sodium carbonate and 300 ml of absolute acetonitrile was refluxed for 7.5 hours, while stirring. Thereafter, the inorganic salts which had separated out were suction-filtered off and washed with acetonitrile, and the mother liquors were collected and concentrated by evaporation. The oily residue N-(β-fluoro-ethyl)-nortropine was dissolved in methylene chloride, and the hydrochloride was prepared in the usual way with hydrogen chloride gas.

White crystals (isopropanol); m.p.: 184°–186° C. (decomp.).

Yield: 48.6 g (87.2% of theory).

The compounds of the present invention, that is, N-(β-fluoroethyl)-nortropine and its acid addition salts, have useful properties. More particularly, they are useful as intermediates for the preparation of N-(β-fluoroethyl)-nortropine benzilate and quaternary salts thereof of the formula

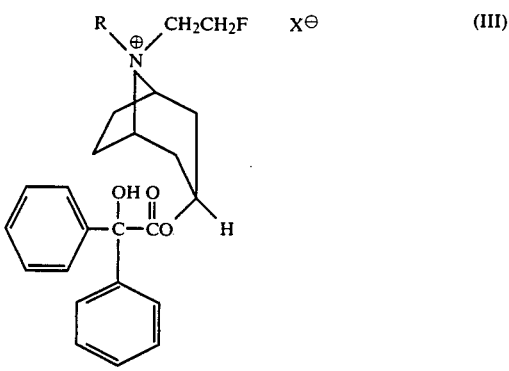

wherein

R is hydrogen or straight or branched lower alkyl, preferably methyl, and $X^\ominus$ is a pharmacologically acceptable anion such as halogen or an organic sulfonic acid radical.

The compounds of the formula III exhibit anticholinergic activity and are especially useful for the treatment of spasm and bronchospasm. These substances are described in German Offenlegungsschrift No. 2,540,633.

The preparation of N-(β-fluoroethyl)-nortropine benzilate from N-(β-fluoroethyl)-nortropine may be effected by methods described in the literature, for example by acylation with benzilic acid imidazolide, as illustrated by the following example.

EXAMPLE 2

N-(β-fluoroethyl)-nortropine benzilate and its hydrochloride 8.4 g (0.03 mol) of benzilic acid imidazolide were added in four portions and at intervals of about 15 minutes to a boiling solution of 5.2 g (0.03 mol) of anhydrous N-(β-fluoroethyl)-nortropine in 50 ml of absolute acetone. The suspension formed thereby was allowed to react further under reflux conditions. If the reaction was still not sufficient, an additional portion of benzilic acid imidazolide was added, while the described procedure was continued.

After a total reaction time of 51 hours, the acetone was distilled off, the oily residue was taken up in methylene chloride, and the solution was exhaustively extracted, first with distilled water and then with dilute hydrochloric acid. The combined acidic aqueous phases were made alkaline, and the reaction product was obtained by extraction with methylene chloride. The combined methylene chloride extracts were dried over sodium sulfate, and after the methylene chloride had been distilled off, the residue was reacted in the usual way with hydrogen chloride gas to form the benzilic acid N-β-fluoroethylenortropine ester hydrochloride.

White crystals (methanol-ether, acetonitrile).
M.p.: 205°–206° C. (decomp.).
Yield: 5.1 g (40.5% of theory).

Using conventional quaternizing agents of the formula $$RX \qquad (IV)$$

wherein R and X have the meanings previously defined, the quaternary compounds of the N-β-fluoroethylnortropine ester of benzilic acid of the formula III are obtained, as described in German Offenlegungsschrift No. 2,540,633.

N-(β-Fluoroethyl)-nortropine itself also has useful pharmacological properties, particularly in the form of its non-toxic, pharmacologically acceptable acid addition salts.

If the compound of formula I or a physiologically acceptable acid addition salt thereof are to be used on their own or in conjunction with other substances as pharmaceutically active substances, they are processed to form pharmaceutical compositions as described in German Offenlegungsschrift No. 2,540,633 (pages 7/8 and 20–24).

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The compound of the formula

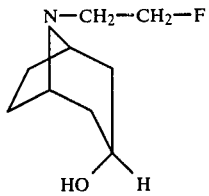

or an acid addition salt thereof.

* * * * *

UNITED STATES PATENT AND TRADEMARK OFFICE
CERTIFICATE OF CORRECTION

PATENT NO. : 4,549,021

DATED : Oct. 22, 1985

INVENTOR(S) : ROLF BANHOLZER

It is certified that error appears in the above-identified patent and that said Letters Patent is hereby corrected as shown below:

Title page, column 2, line 3: "Little" should read -- Littell --.

Signed and Sealed this

Twenty-first Day of January 1986

[SEAL]

Attest:

DONALD J. QUIGG

Attesting Officer

Commissioner of Patents and Trademarks